United States Patent
Catalano (10) Patent No.: US 11,771,588 B2
(45) Date of Patent: Oct. 3, 2023

(54) NON-CONTACT, INFRARED SENSING TEMPERATURE ACTIVATED CONTROLLER FOR ABATEMENT OF EFFECTS OF HOT FLASHES IN A HUMAN BODY

(71) Applicant: Donald J. Catalano, Patterson, CA (US)

(72) Inventor: Donald J. Catalano, Patterson, CA (US)

( * ) Notice: Subject to any disclaimer, the term of this patent is extended or adjusted under 35 U.S.C. 154(b) by 140 days.

(21) Appl. No.: 17/457,613

(22) Filed: Dec. 3, 2021

(65) Prior Publication Data
US 2022/0087859 A1     Mar. 24, 2022

Related U.S. Application Data

(62) Division of application No. 16/568,142, filed on Sep. 11, 2019, now Pat. No. 11,357,663.

(51) Int. Cl.
*A61F 7/00*     (2006.01)

(52) U.S. Cl.
CPC ...... *A61F 7/0085* (2013.01); *A61F 2007/006* (2013.01); *A61F 2007/0064* (2013.01); *A61F 2007/0086* (2013.01); *A61F 2007/0093* (2013.01); *A61F 2007/0096* (2013.01)

(58) Field of Classification Search
CPC ........ A61F 2007/0059; A61F 2007/006; A61F 2007/0063; A61F 2007/0064; A61F 2007/0086; A61F 2007/0093; A61F 2007/0094; A61F 2007/0096; A61F 7/0085; A61B 5/01
See application file for complete search history.

(56) References Cited

U.S. PATENT DOCUMENTS

| | | | | |
|---|---|---|---|---|
| 6,226,996 | B1 * | 5/2001 | Weber | F17C 13/026 236/51 |
| 2010/0286754 | A1 * | 11/2010 | Bly | A61F 7/0085 607/107 |
| 2015/0320588 | A1 * | 11/2015 | Connor | F24F 11/0001 607/104 |

* cited by examiner

*Primary Examiner* — Tigist S Demie
(74) *Attorney, Agent, or Firm* — Ray K. Shahani Attorney At Law

(57) ABSTRACT

A directable, portable appliance in combination with an adjustable set-point digital temperature controller for non-contact remotely monitoring infrared temperatures of a selected area of human skin and activating an electrical fan for directing cooling air over the selected skin areas of individuals experiencing episodes of thermal chaos, i.e., hot flashes.

18 Claims, 9 Drawing Sheets

* spot diameter measured at 90% energy
6:1 distance to spot size ratio.
Optical Field of View

NON-CONTACT, INFRARED SENSING TEMPERATURE ACTIVATED CONTROLLER FOR ABATEMENT OF EFFECTS OF HOT FLASHES IN A HUMAN BODY

RELATED APPLICATIONS

This application is a Divisional Application of Nonprovisional patent application Ser. No. 16/568,142 filed Sep. 11, 2019 entitled "NON-CONTACT, INFRARED SENSING TEMPERATURE-ACTIVATED CONTROLLER FOR ABATEMENT OF EFFECTS OF HOT FLASHES IN A HUMAN BODY", which is incorporated herein by reference in its entirety, and claims any and all benefits to which it is entitled therefrom.

FIELD OF THE INVENTION

The present invention is related to methods and apparatus for controlling a person's body temperature, and more particularly, to a non-contact system for detecting the onset of a hot flash in an individual and activating a proximal air conditioning device in response thereto for abatement thereof.

BACKGROUND OF THE INVENTION

U.S. Pat. No. 6,703,367 issued Mar. 9, 2004 to Garnick teaches methods for treating hot flashes and gynecomastia. This patent is directed to administration of chemical adjuncts but air cooling of the body following detection of the onset of a hot flash using a non-contact IR thermal detector is not described or anticipated.

U.S. Pat. No. 7,9908,688 issued Mar. 22, 2011 to Tompkins teaches a portable ventilation system. This patent is directed to use of a fan to blow air toward a bed to keep the body cool during rest but air cooling of the body following detection of the onset of a hot flash using a non-contact IR thermal detector is not described or anticipated.

U.S. Pat. No. 9,192,244 issued Nov. 24, 2015 to Rand teaches a tunnel generating bed cooling system. This patent is directed to the use of a ventilation system to create a tunnel of cool air in contact with a human body between a mattress and a top sheet but air cooling of the body following detection of the onset of a hot flash using a non-contact IR thermal detector is not described or anticipated.

U.S. Pat. No. 10,172,826 issued Jan. 8, 2019 to Minatelli et al teaches a composition and method to treat and alleviate symptoms of hot flashes in a female subject. This patent is directed to the use of a dietary supplement for treatment of hot flashes but air cooling of the body following detection of the onset of a hot flash using a non-contact IR thermal detector is not described or anticipated.

U.S. Pat. No. 10,179,064 issued Jan. 15, 2019 to Connor teaches wearable environmental control system for predicting and cooling hot flashes. This patent is directed to, inter alia, the use of various types of wearable sensors for modification of a person's environment but air cooling of the body following detection of the onset of a hot flash using a non-contact IR thermal detector is not described or anticipated.

U.S. Pat. No. 10,238,629 issued Mar. 26, 2019 to Set et al teaches methods for reducing the occurrence of hot flashes. This patent is directed to the administration of chemical adjuncts to inhibit the occurrence of hot flashes but air cooling of the body following detection of the onset of a hot flash using a non-contact IR thermal detector is not described or anticipated.

Figure 1A:
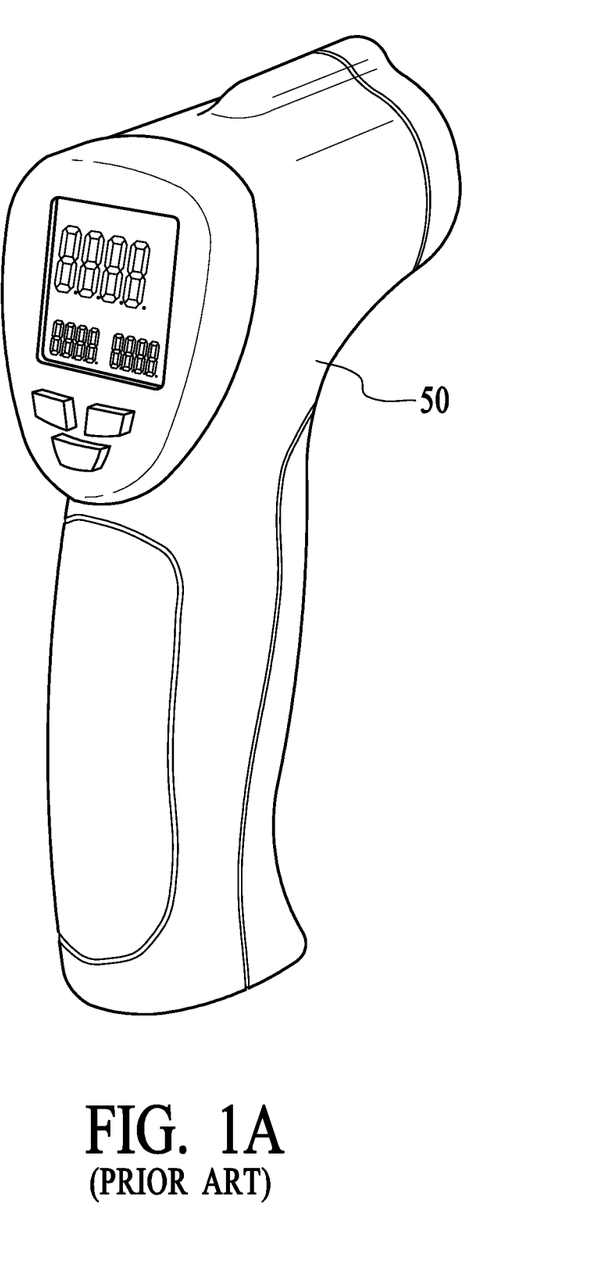
FIG. 1A (prior art) is a perspective view of a hand-held, non-contact infrared thermometer with laser pointer 50.

FIG. 1A (prior art) is a perspective view of a hand-held, non-contact infrared thermometer with laser pointer 50.

One example of a non-contact temperature sensor 50 which can be used to detect the temperature of a human body is the hand-held Wide Range Mini Infrared Thermometer with Laser Pointer, Model No. 42510A made by Extech Instruments, a Flir company. This Infrared thermometer 50 measures and displays non-contact temperature readings up to 1200° F. (650° C.}. The adjustable emissivity feature allows the IR thermometer to measure the temperature of virtually any surface. The built-in laser pointer increases target accuracy while the backlit LCD and handy push buttons combine for convenient, ergonomic operation. Operational functions include adjustable emissivity, high-low alarms, MIN-MAX memory, and trigger-lock test mode. Typically these types of instruments 50 are fully tested and calibrated prior to delivery, and proper use and care of this equipment will typically provide years of reliable service.

Figure 1B:
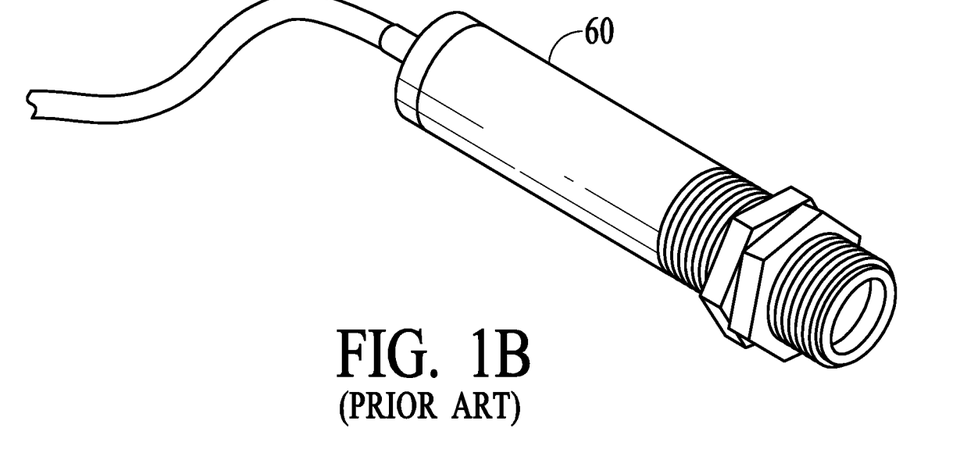
FIG. 1B (prior art) is a perspective view of another example of a non-contact infrared temperature sensor and transmitter 60.

FIG. 1B (prior art) is a perspective view of another example of a non-contact infrared temperature sensor and transmitter 60.

Another example of a non-contact temperature sensor 60 which can be used to detect the temperature of a human body is the OS136 SERIES Miniature Low Cost Non-Contact Infrared Temperature Sensor/Transmitter. The model OS136 series temperature sensor 60 is a low-cost, super-compact infrared transmitter. It measures temperature via non-contact, and provides an analog output proportional to the measured temperature. The OS136 series sensor 60 is offered in two temperature ranges: −18 to 204° C. (0 to 400° F.) and 149 to 538° C. (300 to 1000° F.). The analog output is offered as 4 to 20 mA, 0 to 5 Vdc, 0 to 10 Vdc, 10 mV/Degree C. or F, or K type thermocouple. The unit 60 has a fixed Emissivity of 0.95 which makes it easy to measure temperature, requiring no adjustments during installation and use. The super-compact design, 19 mm OD×89 mm Length (0.75" OD×3.5" L) is ideal to measure temperature in confined, and hard to reach places. The Stainless Steel housing is NEMA-4 rated. The unit 60 comes with a 1.82 m (6') shielded cable as standard.

While the prior art is replete with non-contact temperature scanners, sensors, displays and thermometers, there is nothing in the prior art that teaches or anticipates the use of infrared "non-contact" thermal sensors for automated temperature control of a human being undergoing a rapid increase in body temperature, i.e., for automatic abatement of the adverse effects of "hot flashes".

Figure 1C:
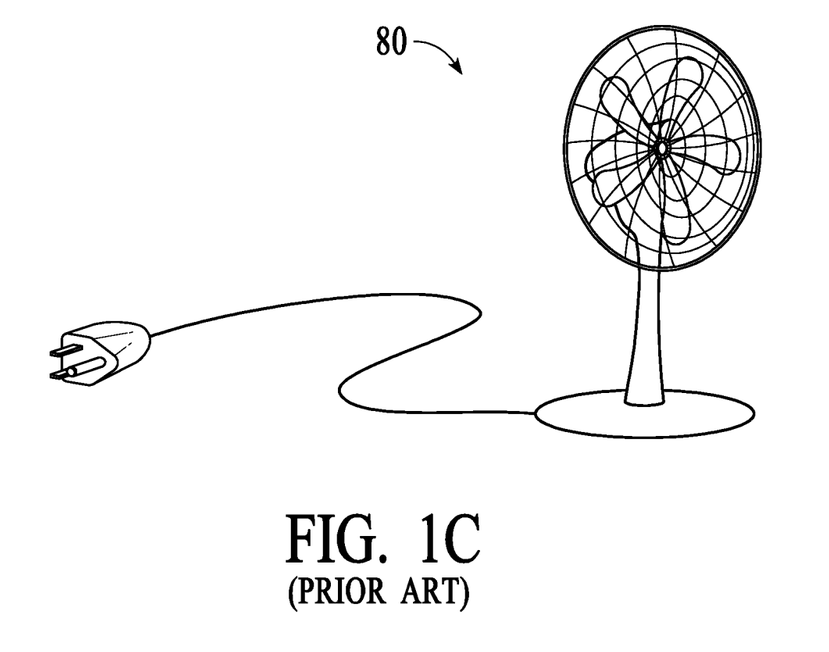
FIG. 1C (prior art) is a perspective view of a typical, alternating current (AC) oscillating or stationary electric fan 80.

FIG. 1C (prior art) is a perspective view of a typical, alternating current (AC) oscillating or stationary electric fan 80.

Finally, electric fans 80 are well known and widely available in a variety of shapes and sizes. It will be understood that the fan 80 used in conjunctions with an embodiment of the present invention can either be portable or permanently mounted to a side table, wall, suspended from the ceiling, or otherwise. Typically electric fans 80 of the prior art have modes for oscillation or can be set up to direct air flow in a single, stationary position. Additionally, electric AC fans 80 can have revolving propellor-type blades, be tubeaxial or vaneaxial, i.e., configured in the shape of a box or tower, or fit within a duct-type space. In another type of electric fan 80, the tube doesn't have any blades inside it, the pedestal of the fan 80 contains a brushless electric motor that takes in air and feeds it into a circular or other shaped emanating tube, and air flows along the inside of the device until it reaches a slit inside the emanating tube. In addition, it will be understood that the AC fan 80 can also have cooled-air and heated air options. Electric fans 80 that contain small air-conditioning and heating units that cool or warm the air being forced to a temperature below or above room-temperature are also well known in the prior art, and their use can be incorporated into the present invention as desired.

Therefore, there currently exists a need in the industry for a device and associated method that gives automatic and symptomatic relief to a person experiencing thermal chaos, otherwise known as a "hot flash", especially while sleeping.

SUMMARY OF INVENTION AND ADVANTAGES

It would be desirable to have a device that automatically produces airflow when a person's body temperature rises above an adjustable set-point temperature which uses a non-contact, temperature sensing probe.

It would be a further advantage to have a device with a simple to use, adjustable digital thermostat for changing the on/off set-point/temperatures.

It would be a further advantage to have a simple to use, adjustable digital thermostat with an illuminated display to enable manual operation, such as temperature set point adjustment, in a dimly lit room or in complete darkness.

The present invention is a device that responds to an increase or decrease in the sensed body temperature to energize or de-energize an AC outlet.

More specifically, the present invention is intended turn-on a cooling fan whenever the user is feeling the effects of a "hot flash" or thermal chaos.

Thus, an embodiment of the present invention is a non-contact, infrared temperature sensing device which, upon sensing an increase or decrease in surface temperature, will activate or deactivate, respectively, an AC powered fan that produces air-flow.

An embodiment of the present invention is a portable, non-contact, infrared, temperature sensing, and power control device which energizes, or de-energizes an integral power relay relative to the temperature of a surface being monitored. The present invention was specifically designed to turn-on a fan to produce airflow in an effort to provide symptomatic relief for people suffering from thermal chaos or hot flashes.

More broadly, the device of the present invention can be used to provide cooling or heating for a person, animal, or object.

With respect to a method of the present invention, a non-contact infrared temperature sensor is pointed or directed toward a surface to be monitored. The temperature sensing electronics associated with an adjustable digital temperature controller are adjusted to a specific set-point temperature, optionally pre-determined by the user, that will activate a power relay in response to a rise in the temperature above the set-point.

With regard to hot flashes, relay activation will take place whenever an increase in temperature beyond the "set-point/ temperature" is detected.

Benefits and features of the invention are made more apparent with the following detailed description of a presently preferred embodiment thereof in connection with the accompanying drawings, wherein like reference numerals are applied to like elements.

DETAILED DESCRIPTION OF THE INVENTION

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

Figure 2A:
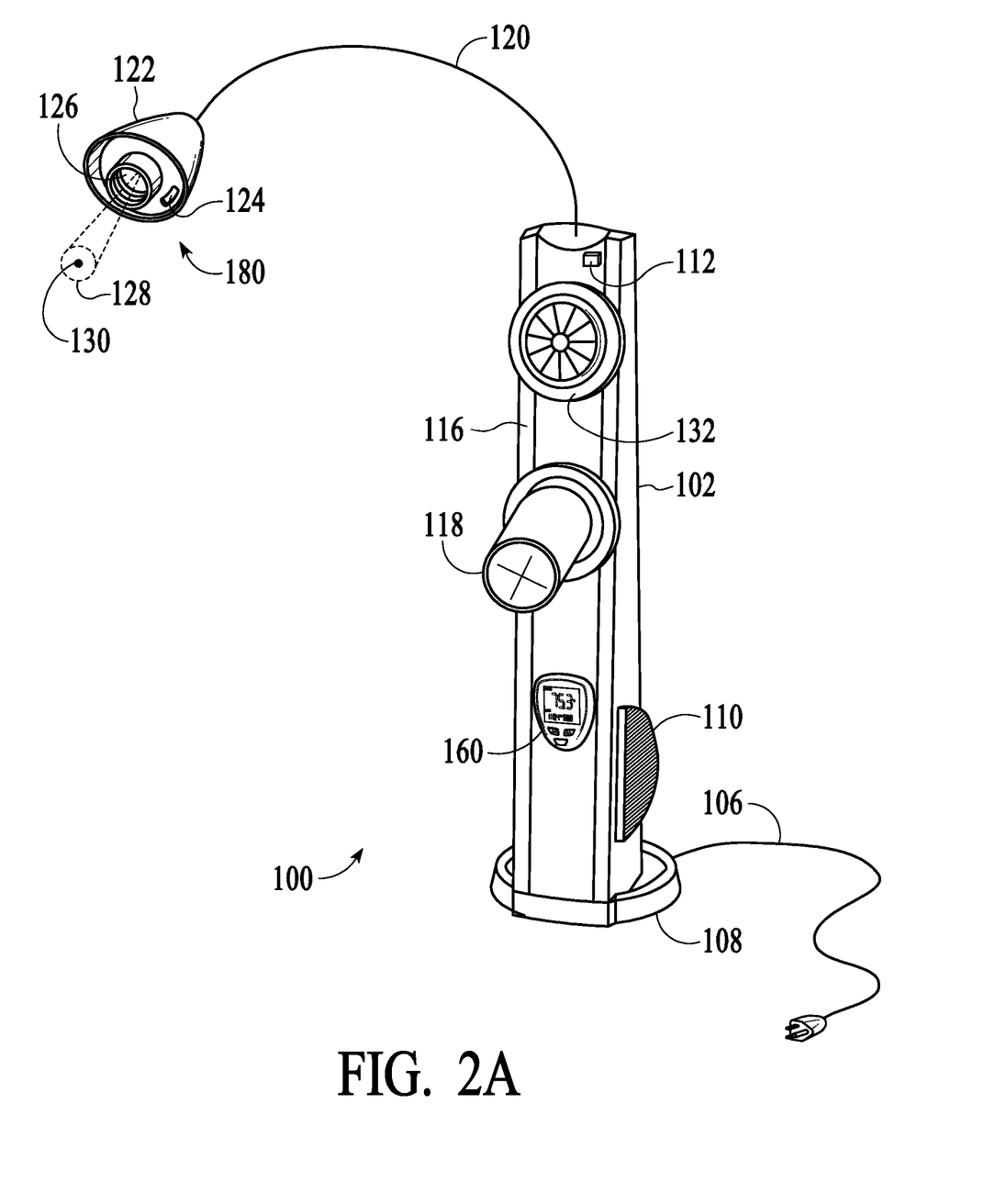
FIG. 2A is a perspective view of an embodiment of the non-contact, infrared temperature controller with air blower 100 of the present invention.

The following is a list of reference numerals and associated elements of the present invention:

- 50 Hand-held, non-contact infrared thermometer with laser pointer (prior art)
- 60 Non-contact infrared temperature sensor and transmitter (prior art)
- 80 Portable or permanent duty alternating current (AC) electric fan or air blower (prior art)
- 100 Non-contact, infrared temperature controller with air blower
- 102 Main system housing
- 104 Base portion
- 106 AC power cord and plug
- 108 Power termination, fusing and distribution strip
- 110 Air inlet (filter)
- 112 Power on/off switch 114 Low voltage power supply for electronics, and on/off switching controls for blower/fan
116 Programmable thermal sensor (thermostat) electronics
118 Air outlet nozzle (fully adjustable)
120 Flexible goose-neck tubing conduit
122 Non-contact IR temperature probe housing
124 Laser/LED
126 Non-contact, infrared temperature probe
128 Probe sensing area
130 Laser or LED targeting pointer
132 Air outlet nozzle (fixed, non-adjustable)
100 Non-contact, infrared temperature controller with air blower
160 Non-contact, infrared temperature controller and display module
162 Scanned temperature read out
164 Set point read out
166 Set point increase
168 Set point decrease
180 Non-contact infrared temperature sensor and transmitter
190 Object person having temperature fluctuation in need of stabilization
192 Exposed body skin surface area
200 Non-contact, infrared temperature controller
204 Base portion
208 Switched AC power output with rising temperature (for cooling)
210 Switched AC power output with falling temperature (for heating)
220 USB port
222 AC power cord and plug
232 Fan cord/plug FIG. 2A is a perspective view of an embodiment of the non-contact, infrared temperature controller with air blower device 100 of the present invention. FIG. 2C is a view of an embodiment of a typical temperature controller and display module 160 of the present invention. FIG. 2D is a perspective view of an embodiment of the non-contact infrared temperature sensor and transmitter 180 of the present invention.

The core components of the device 100 are main system housing 102 and base portion 108, an AC power cord with plug 106, push-buttons 166 and 168 for adjusting the digital temperature controller and display module 160, flexible hollow-steel shaft or gooseneck 120, non-contact infrared temperature sensor 126, air inlet 110, fully adjustable air outlet nozzle 118 and fixed air outlet nozzle 132.

The digital temperature controller and display module 160 displays the scanned or detected temperature 162 as well as the temperature set-point 164. Control buttons 166 and 168 can be manually operated to increase or decrease, respectively, the temperature set-point 164.

The non-contact infrared temperature sensor and transmitter 180 of the present invention comprises the non-contact, infrared temperature sensor 126, the housing 122 within which the temperature sensor 126 is housed, and a laser or LED pointing arrow output 124. The temperature sensor 126 and housing 122 are mounted onto the flexible steel shaft gooseneck 120 so that the orientation of the temperature sensor and transmitter 180 can be selected manually to detect the desired portion of skin 192 on the object 190.

Generally speaking, the non-contact infrared temperature sensor with air blower 100 is configured as follows: All components are mounted within the housing 102 of the device 100. The power cord 106 enters the housing 102 and is intended to be plugged in to AC power from a common household outlet. The adjustable digital temperature controller and display module 160 is adjusted up or down by the user to a specific temperature set-point 164. The adjustable digital temperature controller and display module 160 turns on and turns off air flow through the air outlet nozzles 118 and 132 relative to the set-point temperature 164. The non-contact infrared temperature sensor 126 is mounted within a housing 122 which is attached to the main system housing 102 by the flexible, optimally spiral-wound, hollow steel gooseneck or shaft 120 that provides for a plurality of positioning of the non-contact infrared temperature sensor 126. Additionally the flexible hollow-shaft gooseneck 120 provides a conduit for power and signal wiring between the non-contact infrared temperature sensor 126 and the adjustable digital temperature controller and display module 160.

In use, the non-contact infrared temperature sensor 126 is directed towards exposed body skin surface area 192 of the object's body 190 and provides an analog signal, relative to detected skin 162 temperature, for use by the adjustable digital temperature controller 100. An AC powered fan is located within the main system housing 102 such that when activated, air blows out the air outlet nozzle 118. The adjustable digital temperature controller and display module 160 will turn on the internal fan to provide cooling/airflow from the nozzles 118 and 132 whenever the set-point temperature 164 is exceeded and, conversely, turn-off the fan when the scanned or detected temperature 162 falls below the set-point value 164.

Figure 2B:
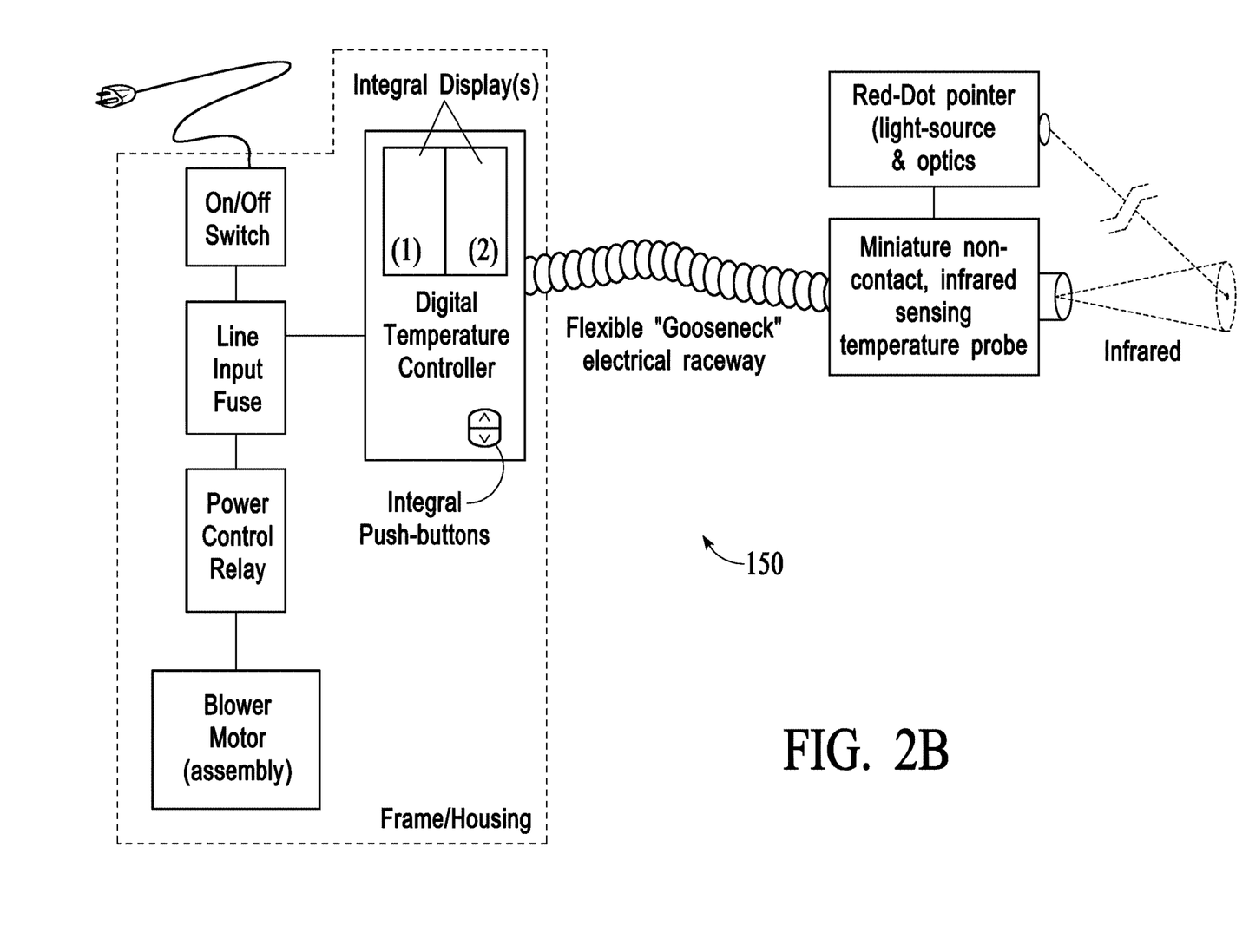
FIG. 2B is a flowchart 150 showing the method of operation and use of the non-contact, infrared temperature controller with blower 100 of the present invention.
Figure 2C:
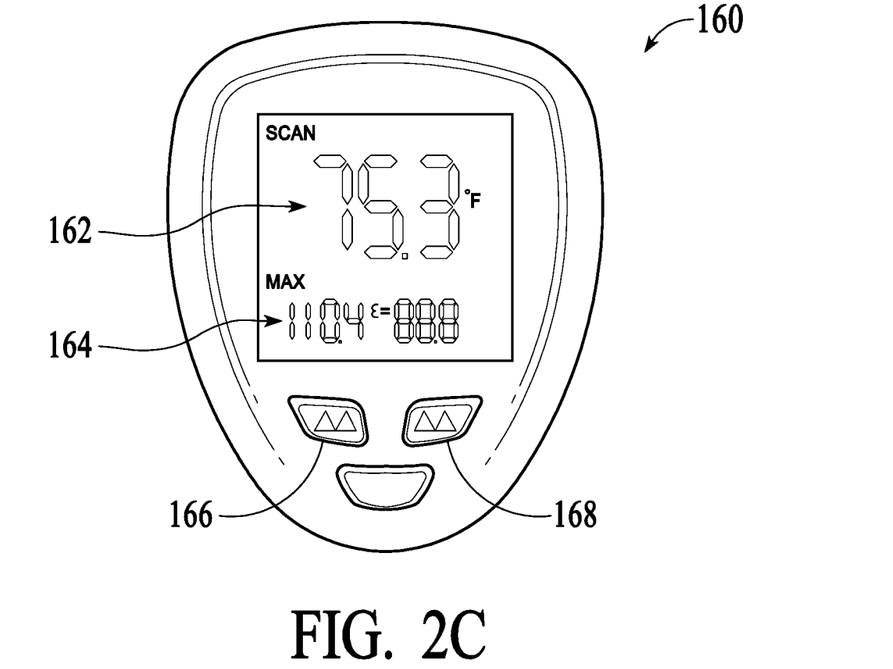
FIG. 2C is a view of an embodiment of a typical temperature controller and display 160 of the present invention.
Figure 2D:
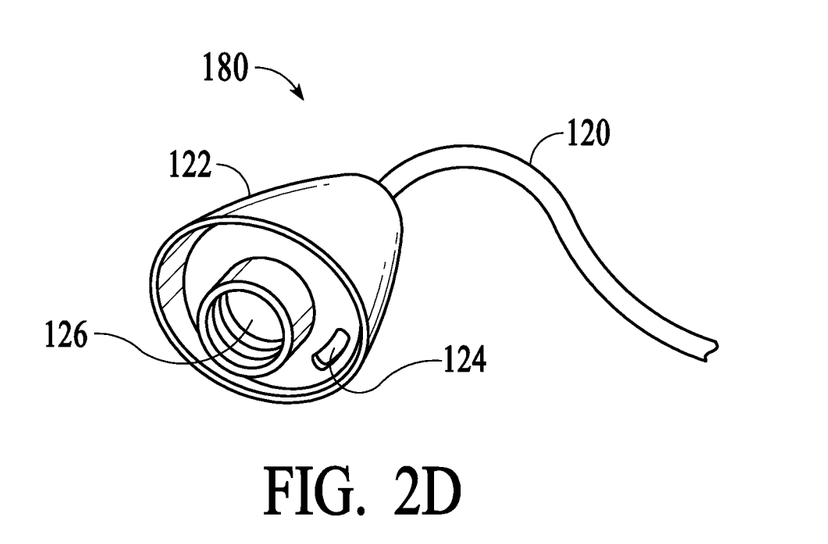
FIG. 2D is a perspective view of an embodiment of the non-contact infrared temperature sensor and transmitter 180 of the present invention.

FIG. 2B is a flowchart 150 showing the method of operation and use of the non-contact, infrared temperature controller with blower 100 of the present invention. The power cord 106 provides AC power to the entire device 100. The frame housing 102 provides a mounting platform for components of the system 100. Power to the device 100 is manually operated and controlled by the on-off switch 112 which connects power to and disconnects power from the device 100. The line input fuse or circuit breaker 108 protects the power cord 106 and the rest of the non-contact, infrared temperature controller with blower 100 from an overload condition and the internal electronics/electrical components from over-current damage.

A power control relay applies power to the blower motor based on the control logic used. In other words, the blower-motor could be made to "turn-on" with a "rising" or a "falling" temperature.

The motorized fan assembly is a fan/blower-motor that produces air-flow. This is part of a larger assembly which allows for the directional control of the air-flow produced. The fully adjustable air-flow nozzle 118 allows a user or object to direct air-flow wherever desired, i.e., airflow emanating from the nozzle 118 in any desired direction, whereas activation of the fixed air-flow nozzle 132 allows a user or object to direct air-flow at a operative location in a fixed direction and at an operative distance from the nozzle 132.

The "up" temperature button 166 and the "down" temperature button 168 of the digital temperature controller and display 100 adjusts the "turn-on" or "turn-off" temperature "set-point" 164.

The flexible "gooseneck" electrical raceway 120 carries power and signal wiring to/from the temperature sensor 126, and allows for unlimited positioning of the sensor 126 by the user 190 as it maintains whatever position it is set to.

The miniature non-contact, infrared temperature sensor 126 measures the temperature at the target skin area 192 using non-contact, infrared temperature sensing technology.

The red dot pointer 130 comprises a light source and optics 124. This system allows for precise positioning in the "optical field of view" 128 of the sensor 126. While not required, this dot pointer 128 allows for easy positioning of the sensor 126 on the surface 192 of a person or object 190.

Figure 3A:
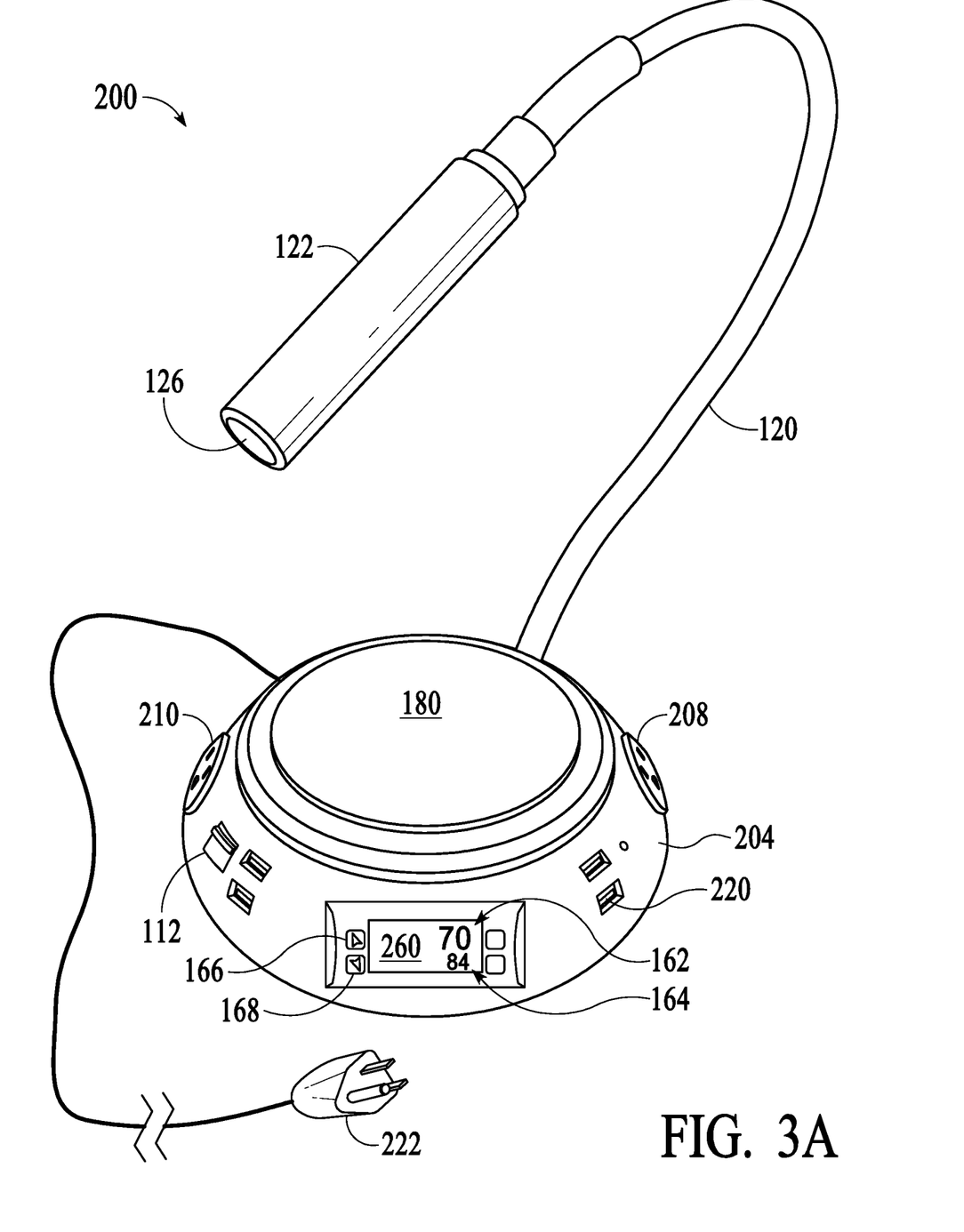
FIG. 3A is a perspective view of an embodiment of another non-contact, infrared temperature controller 200 of the present invention.

FIG. 3A is a perspective view of an embodiment of another non-contact, infrared temperature controller 200 of the present invention.

The core components of the device 200 are main system housing and base portion 204, an AC power cord with plug 222 power on/off switch 223, flexible hollow-steel shaft or gooseneck 120, sensor housing 122, and non-contact infrared temperature sensor 126. The digital temperature controller and display module 260 displays the scanned or detected temperature 162 as well as the temperature set-point 164. Control buttons 166 and 168 can be manually operated to increase or decrease, respectively, the temperature set-point 164.

The non-contact infrared temperature sensor 126 also optionally comprises a laser or LED dot pointer arrow output (not shown). The temperature sensor 126 and housing 122 are mounted onto the flexible steel shaft gooseneck 120 so that the orientation of the temperature sensor 126 can be adjusted manually to detect the temperature of a desired portion of skin 192 on the object 190.

Finally, switched AC power outlet 208 is activated when the detected temperature 162 is greater than the set-point temperature 164, and switched AC power outlet 210 is activated when the detected temperature 162 is lower than the set-point temperature 164.

Generally speaking, the non-contact infrared temperature sensor 200 is configured as follows: Electronic components are mounted within the housing and base portion 204 of the device 200. A power cord 222 enters the housing and base portion 204 and is intended to be plugged in to an AC power source such as from a common household outlet. The position of the flexible gooseneck 120 coupled to the digital temperature controller and display module 260 and a specific temperature set-point 164 is manually adjustable by the user. The adjustable digital temperature controller and display module 260 activates either switched AC power outlet 208 or switched AC power outlet 210, depending upon the measured temperature of the object 190 and the value of the set-point temperature 164. Thus, the controller electronics inside the main system base portion 204 simultaneously activates and deactivates, respectively, the switched AC power outlets 208 and 210 when the temperature detected by the sensor 126 rises above or falls below the set-point temperature 164.

An AC powered fan or air-conditioning unit (not shown) can be plugged in to switched AC outlet 208 such that when activated, the fan or air conditioning unit will initiate cooling of the object 190. Alternatively, when a heating unit such as a resistive heating coil or hot air blower is plugged into switched AC power outlet 210 and the outlet 210 is activated, the object 190 will be warmed.

The non-contact infrared temperature sensor 126 is directed towards exposed body skin surface area 192 of the object 190 and provides an analog signal, relative to detected skin 162 temperature, for use by the adjustable digital temperature controller 200. An AC powered fan is plugged into the AC switched power outlet 208 of the main system housing 204 such that when activated, cooling air blows out the fan. The adjustable digital temperature controller 260 will turn on the fan to provide cooling/airflow whenever the set-point temperature 164 is exceeded and, conversely, turn-off the fan when the scanned or detected temperature 162 falls below the set-point value 164.

As mentioned above, an embodiment of the present invention 200 has an illuminated digital temperature sensor controller and display module 260. The illuminated display 260 makes it very convenient to turn the device on and off, to make a temperature set point adjustment, or otherwise adjust the temperature controlling device 200 in a dimly lit room or in complete darkness. Given the frequency of events of thermal chaos at night while sleeping or otherwise, an illuminated display module 260 is helpful for accurately operating the device in low light or other periods of darkness.

Figure 3B:
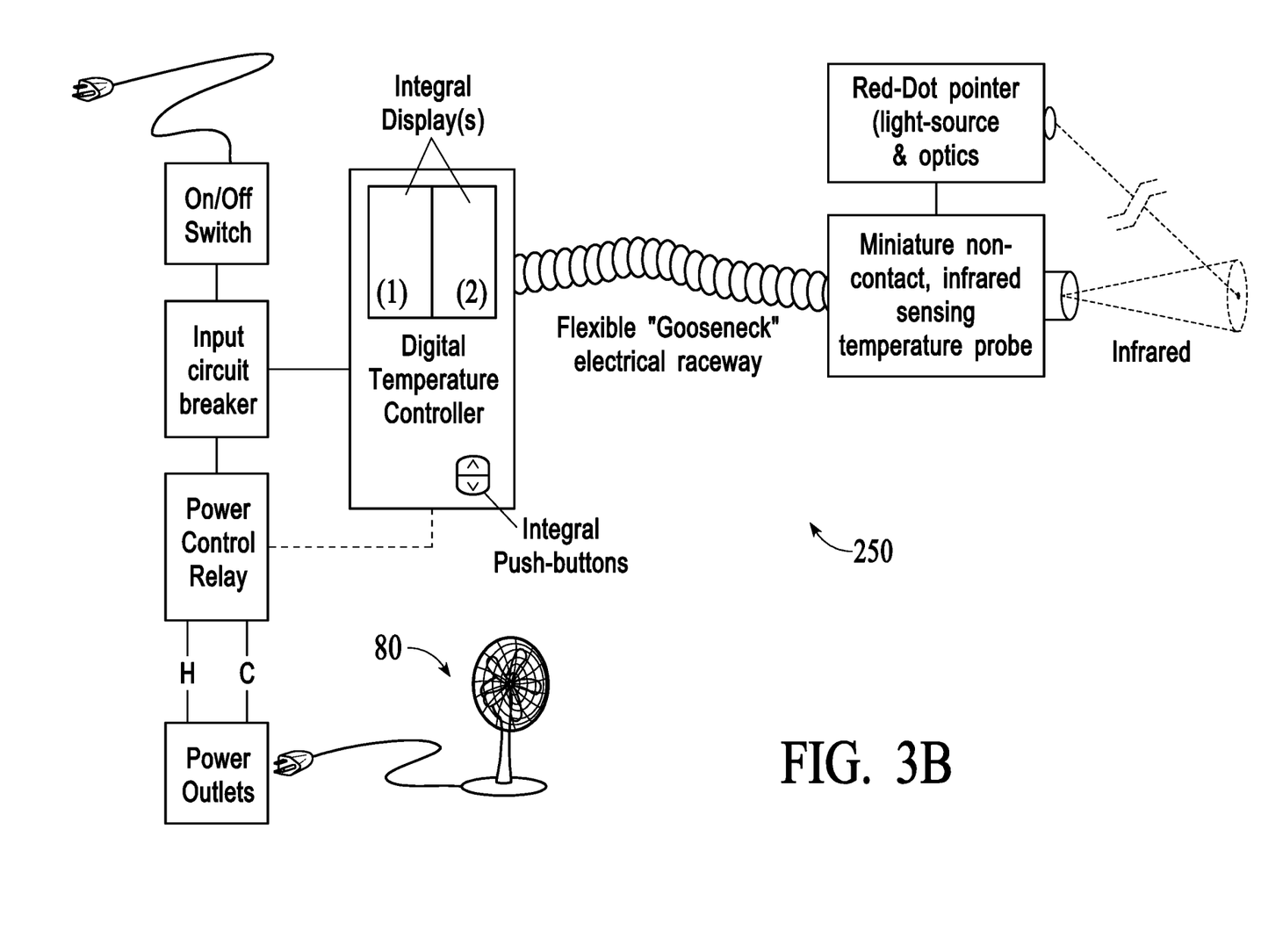
FIG. 3B is a flowchart 250 showing the method of operation and use of the non-contact, infrared temperature controller 200 of the present invention.

FIG. 3B is a flowchart 250 showing the method of operation and use of the non-contact, infrared temperature controller 200 of the present invention. The power cord 106 provides power to the device 200, and also supplies "line power" to any "load/fan" connected to the device 200. The base housing 204 provides a mounting platform for components of the system 200. Power to the device 200 is manually operated and controlled by the on-off switch which connects power to and disconnects power from the device 200. The input fuse or circuit breaker automatically disconnects power from the device 200 and protects the power cord from an overload condition and the internal electronics/electrical components from over-current damage.

A power control relay applies power to the switched power outlets 208 and 210 based on the control logic used by a digital temperature controller. Switched power outlets 208 and 210 are available for use. One switched power outlet 208 is for cooling, i.e., power will be output with a rising measured temperature 162. One switched power outlet 210 is for heating, i.e., power will be output when a falling temperature 162 is detected. It will be understood that a power cord attached to a third-party fan or heating unit can be plugged in to Switched Power Outlets 208 and 210, depending upon desired use of the system 200.

The adjustable digital temperature controller and display module 260 is part of the digital temperature controller. The module 260 consists of 2 displays. The display of the actual, real-time measured temperature 162 is obtained from the non-contact temperature probe 126. The second display is the set-point temperature 164. The set-point display 164 is adjustable using the integral increase 166 and decrease 168 push-buttons on the front face of module 260.

The flexible "gooseneck" electrical raceway 120 carries power and signal wiring to/from the temperature sensor 126, and optimally allows for unlimited positioning of the sensor 126 by the user/object 190.

The miniature non-contact, infrared temperature sensor 126 measures the temperature at the target skin area 192 using non-contact, infrared temperature sensing technology.

The red dot pointer comprises an LED or laser light source 124 and optics. This system allows for precise positioning in the "optical field of view" 128 of the sensor 126. While not required, this dot pointer 124 allows for easy positioning of the sensor on the surface of the object 190.

In an embodiment of the present invention 200, an indicator light such as a solid or flashing red light could indicate the condition where the measured temperature 162 of the object 190 is at or is greater than the setpoint temperature 164 and the switched power outlet 208 is activated. The indicator light could also be solid or flashing green light when the measured temperature 162 is at or is lower than the setpoint temperature 164. In addition, it will be understood that an audible signal could indicate the condition where the measured temperature 162 of the object 190 is greater than, equal to or less than the setpoint temperature 164.

It will be understood that the adjustable set-point, non-contact infrared sensing digital temperature controller 100 and 200 of the present invention is for non-contact remotely monitoring infrared temperatures of a selected area of human skin 192 and activating an electrical fan 80 for directing cooling air over the selected skin areas 192 of individuals 190 experiencing episodes of thermal chaos, i.e., hot flashes. However, the present invention can also be used for non-contact remotely monitoring infrared temperatures of a selected area of human skin and remotely activating the electrical fan 80 for directing heating air over the selected skin areas of individuals experiencing chills or other cold-flash episodes. The signal transmitted from the infrared sensing temperature probe 126 is an analog voltage. The digital temperature controller 160 converts this analog signal to a digital format for processing by the integral microcontroller. The resolved data is sent to the display driver for illuminating the LED display. Furthermore, the digital signal representing the detected temperature 162, setpoint 164 and control command input and output can be made available through a 2-pin RS485 serial communication port and communication could also be accomplished using USB, Ethernet, Bluetooth or any appropriate communications protocol. Real-time programming changes to hi/low set-points, setpoint alarms, and display attributes can be made via the communications port.

Additionally, in an embodiment of the non-contact infrared sensing digital temperature controller 200 of the present invention, the condition where the measured temperature 162 of the object 190 is greater than, equal to, or less than the setpoint temperature 164 could be monitored from a significant distance using Wifi, an RF coupled remote receiver or other wireless communications protocol that could activate an indicator light, an audible signal, or a tactile alert device. This embodiment would be useful for monitoring and manually controlling the temperature of the object 190 from a distant location, such as a nurse's station, doctor's office, caretaker's remote location, etc. In this case, digital signals corresponding to the measured temperature 162 and the setpoint temperature 164 of the sensor 126 of the non-contact infrared sensing digital temperature controller 200 can be transmitted a more significant distance away from the object 190 using Wifi, an RF coupled remote receiver or other wireless communications protocol so that a nurse, doctor, or other healthcare professional or caretaker can manually observe, monitor, adjust or otherwise control operation of the electric fan 80 or other temperature cooling or heating device.

Figure 3C:
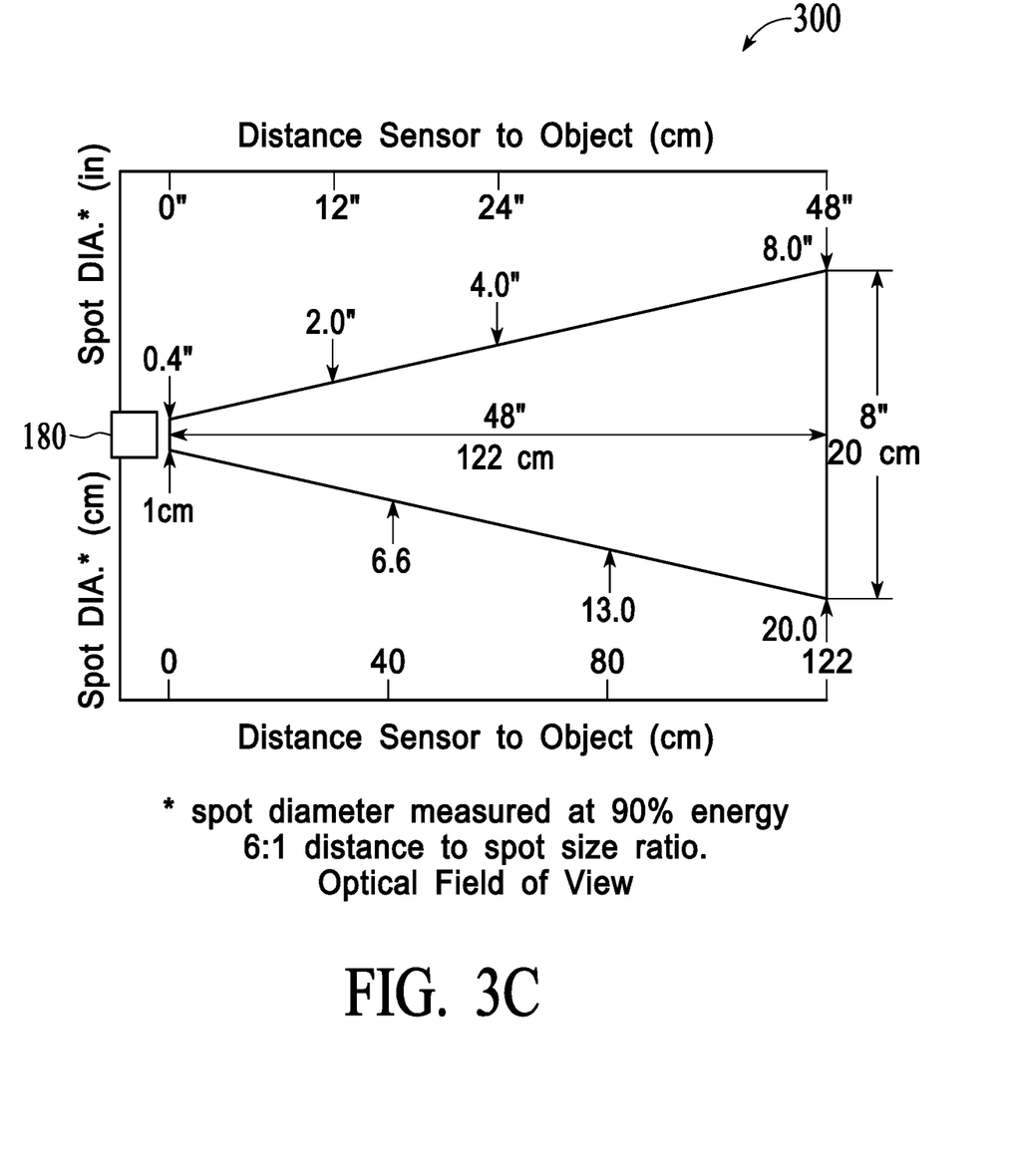
FIG. 3C is a graph 300 showing the relationship between the distance between the infrared temperature sensor and transmitter 180 of the present invention and the object and the diameter of the spot on the object.

FIG. 3C is a graph 300 showing the relationship between the distance from the infrared temperature sensor and transmitter 126 of the present invention and the Object being measured 190 on the one hand, and the diameter of the spot 128 on the object 190 on the other hand. The data shown in FIG. 3C is representative and would vary based upon the type of non-contact infrared thermometer probe selected for use with the present invention. Data representing the distance between the sensor 126 and the Object 190 is plotted on the x-axis, while data representing the diameter of the spot 128 is shown plotted along the y-axis. In the particular sensor 126 used in this graph, an output spot 128 having a diameter of 1 cm/0.4 inches expands to 20 cm/8 inches over the distance of 122 cm/48 inches.

Figure 4:
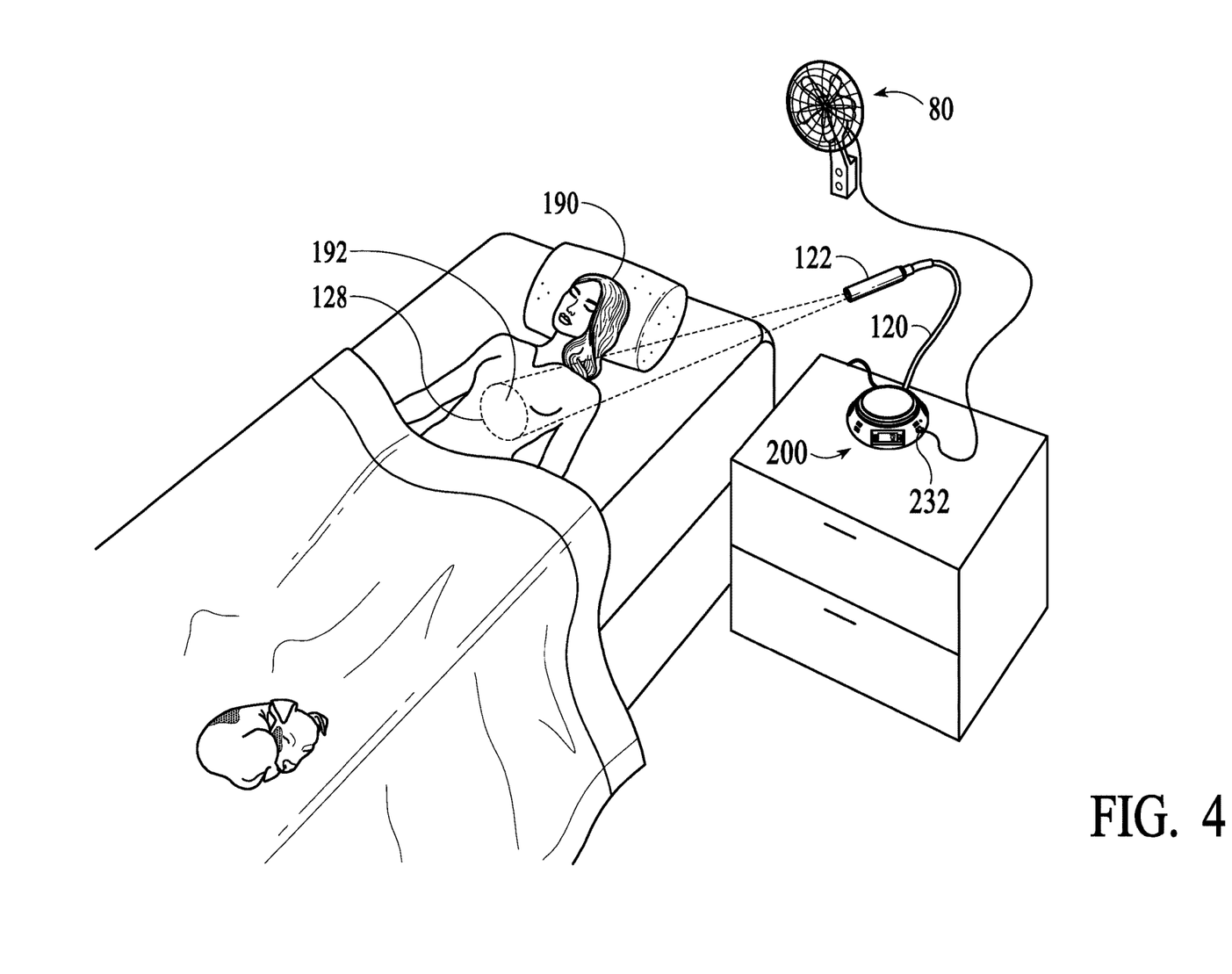
FIG. 4 is a perspective view showing a method of use of the non-contact, infrared temperature controller 200 of the present invention.

FIG. 4 is a perspective view showing a method of use of the non-contact, infrared temperature controller 200 of the present invention.

Method of Use

It should be noted that the present invention was developed for use by woman or men who suffer from hot flashes, i.e., thermal chaos, experienced at any time but particularly while at rest, in bed or asleep. It will be understood, however, that the present invention can be used for numerous purposes where "non-contact" temperature sensing and control applications are preferred.

With respect to the associated method of use of the non-contact, infrared temperature activated controller device 200, the following core steps are followed:

In a first step, the power cord 222 of non-contact, infrared temperature activated controller device 200 is plugged into a common, household AC outlet.

In a second step, the plug 232 of any AC powered oscillating cooling fan or cooling air blower unit 80 is plugged in to switched outlet 208 of the device base-housing 204.

In a third step, the cooling fan unit 80 can be adjusted to a desired speed and direction of air-flow.

In a fourth step, the non-contact, infrared temperature sensor 126 is pointed or directed towards any exposed surface 192, which would typically be a portion of exposed bare skin of the torso, arm, or any other exposed area of a person or other subject 190.

In a fifth step, the user 190 or other operator manually adjusts the digital temperature controller 200 to a desired set-point-temperature 164 until the cooling fan unit 80 turns on, and then the user 190 adjusts the set-point temperature 164 to just below the point at which the fan 80 turns on, typically 1 or 2 degrees lower. Thus, when the set-point temperature 164 is adjusted, any increase in measured temperature 162 of the subject 190 above the set-point temperature 164 will cause the cooling fan unit 80 to turn-on and provide air-flow cooling. Conversely, when the measured temperature 162 of the subject 190 falls below the set-point temperature 164, the cooling fan unit 80 will again turn-off.

It will be understood that while the non-contact, infrared temperature activated controller device 200 of the present invention can be used for cooling the subject 190 upon the onset of a hot flash, the non-contact, infrared temperature activated controller device 200 can also be used for heating the subject 190 upon a decrease of the measured temperature 162 below the temperature set point 164. In this case, the AC-cord of a heating unit (not shown) would be plugged into the switched outlet 210. When the non-contact sensor 126 measures a temperature 162 at the skin surface area 192 of the subject 190 that is below the temperature set point 164, the switched outlet 210 would be activated resulting in the operation of the heating unit to increase the body temperature of the subject 190. At the time the measured temperature 162 of the subject 190 rises above the set point temperature 164, the switched outlet 210 would be deactivated and the heating unit would turn off.

It will be understood that there are potentially many different applications in many different industries for the non-contact, infrared temperature activated controller device 100 or device 200 of the present invention. Various applications include cooling of cooked or raw food, meat, fruits and vegetables in storage, point of sale, restaurants, commercial or residential kitchens. Cooling of products or people in hot environments as well as heating of products or people in cool environments is possible. Industrial applications include but are not limited to manufacturing processes, agricultural processes, painting processes, semiconductor fabrication, biotechnology manufacturing processes, welding and soldering, biological systems control, medical and other therapeutic processes, etc.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

I claim:

1. A portable, non-contact, infrared temperature activated cooling device for minimizing discomfort of an individual experiencing a hot flash, the device comprising: a cooling fan with blower motor for generating cooling air when activated; a power control relay for activating the cooling fan blower motor; a directable, non-contact, infrared sensing temperature transmitter probe for remotely sensing temperature of a target skin area of a human-being prone to experiencing hot or cold skin surface temperature variations; and a digital temperature controller in which a desired setpoint temperature can be set, wherein when the sensing probe senses a temperature of the target skin area at a temperature above the setpoint, cooling air is generated for cooling the individual until the temperature of the target skin area falls below the temperature setpoint of the digital temperature controller; wherein the non-contact infrared sensing temperature transmitter probe has an optical field of view having a ratio of distance (D) to sensing spot diameter (S) of the appliance at 90% energy of 6:1.

2. The portable cooling device of claim 1 wherein the non-contact infrared sensing temperature transmitter probe has an optical field of view smaller than the target skin area.

3. The portable cooling device of claim 1 wherein the non-contact infrared sensing temperature transmitter probe has an optical field of view of between about 2 and 12 inches in diameter when located between about 2 and 10 feet from the target object.

4. The portable cooling device of claim 1 wherein the non-contact infrared sensing temperature transmitter probe has an optical field of view of between about 4 and 10 inches in diameter when located between about 2 and 10 feet from the target object.

5. The portable cooling device of claim 1 wherein the non-contact infrared sensing temperature transmitter probe has an optical field of view of about 6 to 8 inches in diameter when located about 4 feet from the target object.

6. The portable cooling device of claim 1 further including:
a housing base that contains the cooling fan and blower motor, and
a hollow, flexible electrical wiring raceway support arm mechanically and electrically coupling the non-contact, infrared sensing temperature transmitter probe to the housing base.

7. The portable cooling device of claim 6 wherein the housing base has sufficient mass for anchoring the flexible, electrical wiring raceway support arm and allowing manual adjustment for positioning the optical field of view of the probe to within the target skin area of the human being.

8. The portable cooling device of claim 1 further including;
a conventional AC electrical controller within the housing base providing a low voltage power source electronic controller for powering the non-contact infrared sensing temperature transmitter probe.

9. The portable cooling device of claim 1 wherein the digital temperature controller further comprises:
a dual-LED that displays an actual temperature readout and provides means for manually setting real-time higher-on and lower-off temperature set points.

10. The portable cooling device of claim 1 further comprising the following:
a power on-off switch;
a line input fuse or other circuit breaking device for preventing power overloading conditions;
a digital temperature display for displaying the temperature of the target skin area measured by the temperature sensing probe;
a thermostat controller for manually adjusting the setpoint of the digital temperature controller; and
a red dot light source and pointer optics for producing a red dot on the portion of the individual's body where the temperature is to be sensed.

11. The portable cooling device of claim 10 wherein the thermostat controller is illuminated to facilitate manual operation in darkness or other low-light conditions.

12. The portable cooling device of claim 10 wherein the thermostat controller comprises a manually operated control knob.

13. The portable cooling device of claim 10 wherein the thermostat controller comprises manually operated control push-buttons.

14. The portable cooling device of claim 1 wherein the signal transmitted from the non-contact, infrared sensing temperature probe is an analog voltage and the electrical controller converts this analog signal to a digital format for processing.

15. The portable cooling device of claim 14 wherein the resolved analog signal in digital format is sent to a display driver for illuminating a digital temperature display.

16. The portable cooling device of claim 14 wherein the resolved analog signal in digital format represents the detected temperature setpoint and a control command input and output is made available through a 2-pin RS485 serial communication port such that real-time programming changes to hi/low setpoints, setpoint alarms, and display attributes can be made via the communications port.

17. The portable cooling device of claim 14 wherein the resolved analog signal in digital format represents the detected temperature setpoint and a control command input and output is made available through using USB, Ethernet, Bluetooth or any appropriate communications protocol such that real-time programming changes to hi/low setpoints, setpoint alarms, and display attributes can be made via the communications protocol.

18. The portable cooling device of claim 17 wherein the Wifi, RF coupled remote receiver, or other wireless communications protocol activates an indicator light, an audible signal, or a tactile alert device at a location distant from the temperature activated controller.

\* \* \* \* \*